United States Patent [19]

Rudolph et al.

[11] Patent Number: 5,453,363
[45] Date of Patent: Sep. 26, 1995

[54] PROCESS FOR THE ACTIVATION OF T-PA OR ING AFTER GENETIC EXPRESSION IN PROKARYOTES

[75] Inventors: Rainer Rudolph, Regensburg; Stephan Fischer, Weilheim; Ralf Mattes, Oberhausen, all of Germany

[73] Assignee: Boehringer Mannheim GmbH, Mannheim-Waldhof, Germany

[21] Appl. No.: 206,044

[22] Filed: Mar. 2, 1994

Related U.S. Application Data

[63] Continuation of Ser. No. 942,370, Sep. 9, 1992, abandoned, which is a continuation of Ser. No. 498,500, Mar. 23, 1990, abandoned, which is a continuation-in-part of Ser. No. 76,207, filed as PCT/EP86/00610, Oct. 23, 1986, abandoned.

[30] Foreign Application Priority Data

Oct. 23, 1985 [DE] Germany .......................... 35 37 708.9

[51] Int. Cl.⁶ ...................... C07K 14/745; C07K 16/00; C12P 21/02; C12N 15/00
[52] U.S. Cl. ...................... 435/69.1; 435/71.2; 435/69.5; 435/69.6; 435/849; 435/877; 530/381; 530/387.1; 530/402; 530/404; 530/412; 530/414; 935/49
[58] Field of Search .................. 435/59, 60, 61, 435/66, 69.1, 71.2, 72, 172.1, 172.3, 212, 217, 226, 252.3, 240.21, 69.5, 69.6, 849, 877; 530/402, 404, 412, 414, 381, 387.1; 935/49

[56] References Cited

U.S. PATENT DOCUMENTS

| | | | |
|---|---|---|---|
| 4,432,895 | 2/1984 | Tarnowski | 530/351 |
| 4,511,502 | 4/1985 | Builder et al. | 530/417 |
| 4,766,075 | 8/1988 | Goeddel et al. | 435/240.2 |

FOREIGN PATENT DOCUMENTS

| | | |
|---|---|---|
| 0114506 | 8/1984 | European Pat. Off. . |
| 228862 | 7/1987 | European Pat. Off. . |
| 303251 | 2/1989 | European Pat. Off. . |
| 8403711 | 9/1984 | United Kingdom . |

OTHER PUBLICATIONS

Harris, T. J. R. et al., Mol. Biol. Med. 3:279–292, 1986.
Wolf–Dieter Schleuning in Biotechnology in Clinical Medicine edited by Albertini, Alberto et al., Raven Press Ltd., New York 1987.
Odorzynski, Thomas W. and Albert Light, J. Biol. Chem., 254 No. 10:4291–4295, May 25, 1979.
Yu–Chang John Wang and Musetta A. Hanson, J. Parenteral Science and Technology, vol. 42 (1988) S3–S28.
Freedman and Hillson (1980) the Enzymology of Post–translational Modification of Proteins, vol. 1, pp. 157–212, Chap. 4 "Formation of Disulphide Bonds".
Rudolph, R. et al., Hoppe–Seyler's Z. Physiol. Chem., vol. 364 pp. 813–820, Jul. 1983.
Trexler, M., et al. Biochemica et Biophysica Acta, vol. 787, pp. 275–280, 1984.
Orsini, G., et al. Jour. of Biol. Chem., vol. 253, pp. 3453–3458, 1978.
Cabilly, S., et al. Proc. Natl. Acad. Sci. USA, vol. 81, pp. 3273–3277, Jun. 1984.

*Primary Examiner*—Jacqueline M. Stone
*Assistant Examiner*—Brian R. Stanton
*Attorney, Agent, or Firm*—Felfe & Lynch

[57] ABSTRACT

A process for the activation of t-PA or IgG after expression in prokaryotes is described. The process includes cell digestion, solubilization under denaturing and reducing conditions and activation under oxidizing conditions in the presence of GSH/GSSG.

20 Claims, 7 Drawing Sheets

FIG. 3A

```
   1  TTCATGGATATTGTGCTAACTCAGTCTCCAGCCACCCTGTCTGTGACTCCAAGAGATAGC
  61  GTCAGTCTTTCCTGCAGGCCAGCCAAAGTATTAGCAACCTACACTGGTATCAACAA
 121  AAATCACATGAGTCTCCAAGGCTTCTCATCAAATATGCTTCCCAGTCTCCATCTCTGGATC
 181  CCCTCTAGGTTCAGTGGCAGTGGATCAGGGACAGATTTCACTCTCAGTATCAACAGTGTG
 241  GAGACTGAAGATTTTGGAATGTATTTCTGTCAACAGAGTAACAGCTGCCTCTCACGTTC
 301  GGTGCTGGGACCAAGCTGGAGCTGAAACGGGCTGATGCTGCACCAACTGTATCCATCTTC
 361  CCACCATCCAGTGAGCAGTTAACATCTGGAGGTGCCTCAGTCGTGTGCTTCTTGAACAAC
 421  TTCTACCCCAAAGACATCAATGTCAAGTGGAAGATTGATGGCAGTGAACGACAAAATGGC
 481  GTCCTGAACAGTTGGACTGATCAGGACAGCAAAGACAGCACCTACAGCATGAGCAGCACC
 541  CTCACGTTGACCAAGGACGAGTATGAACAGCACAACAGCTATACCTGTGAGGCCACTCAC
 601  AAGACATCAACTTCACCCATTGTCAAGAGCTTCAACAGGAATGAGTGTTAGAGACAAAGG
 661  TCCTGAGACGCCACCACCAAAGCTTCTGTTTTGGCGATGATAAAACAGAATTTGCCTGGCGCAGTA
 721  TACAGATTAAATCAGAAGCAGAAGCGGTCTGATAAAACAGAAGTGAAACGCCGTAGCGCCGATG
 781  GCGCGGTGTGGGGTCTCCCCATGCGAGAGTAGGGAACTGCCAGGCATCAAATAAAACGAAAG
 841  GTAGTGTGGGGATCTCAGTGGCCCTTTCGTTTTATCTGTTTGTTGCGGTGAACGCTCCTG
 901  GCTCAGTCGAAAGATCGGGCCTTTCGTTTTATCTGTTTGAACGTTGAAGCAACGCCCGGAGGTGG
 961  AGTAGGACAAATCCGCGGACGCCCCGCCATAAACTGCCAGGCATCAAATTAAGCAGAAGGCCATCCTGACG
1021  CGGGCAGGAGCCTTTTGCGTTTCTACAAACTCTTTTGTTATTTTCTAAATACATTCAAATAT
1081  GATGGCCTTTTGCGTTTCTACAAACTCTTTTGTTATTTTCTAAATACATTCAAATAT
1141  GTATCCGCTCATGAGACAATAACCCTGATAATGCTTCAATATATTGAAAGGAAGAG
1201  TATGAGTATTCAACATTTCCGTGTCGCCCTTATTCCCTTTTTTGCGGCATTTTGCCTTCC
1261  TGTTTTTGCTCACCCAGAAACGCTGTGGATCGAACTGGATCTCAACAGGTAAGATCGAGTTTCGCCC
1321  ACGAGTGGTTACATCGAACTGGATCTCAACAGCGGTAAGATCCTTGAGAGTTTTCGCCC
1381  CGAAGAACGTTTTCCAATGATGAGCACTTTAAAGTTCTGCTATGTGGCGCGGTATTATC
1441  CCGTGTTGACGCCGGGCAAGAGCAACTCGGTCGCCGCATAACTATTCTCAGAATGACTT
1501  GGTTGAGTACTCACCAGTCACAGAAAAGCATCTTACGGATGGCATGACAGTAAGAGAATT
1561  ATGCAGTGCTGCCATAACCATGAGTGATAACACTGCGGCCAACATGGGGATCATGTAACTCGCCT
1621  CGGAGGACCGAAGGAGCTAACCGCTTTTTTGCACAACATACCAAACGACGAGCGTGACACCACGAT
1681  TGATCGTTGGGAACCGGAGCTGAATGAAGCCATACCAAACGACGAGCGTGACACCACGAT
```

FIG. 3B

```
1741  GCCTGTAGCAATGGCAACAACGTTGCGCAAACTATTAACTGGCGAACTACTTACTCTAGC
1801  TTCCCGGCAACAATTAATAGACTGGATGGAGGCGGATAAAGTTGCAGGACCACTTCTGCG
1861  CTCGGCCCCTTCCGCTGGCTGGTTGTTATTGCTGATAAATCTGGAGCCGGTGAGCGTGGTC
1921  TCGGGTATCATTGCAGCACTGGGGCAGGCCAGATGGTAAGCCCCTCCCGTATCGTAGTTATCTA
1981  CACGACGGGAGTCAGGCAACTATGGATGAACGAAATAGACAGATCGCTGAGATAGGTGC
2041  CTCACTGATTAAGCATTGGTAACTGTCAGACCAAGTTTACTCATATATACTTTAGATTGA
2101  TTTAAAACTTCATTTTTAATTTAAAAGGATCTAGGTGAAGATCCTTTTGATAATCTCAT
2161  GACCAAAATCCCTTAACGTGAGTTTTCGTTCCACTGAGCGTCAGACCCCGTAGAAAAGAT
2221  CAAAGGATCTTCTTGAGATCCTTTTTTTCTGCGCGTAATCTGCTGCTTGCAAACAAAAAA
2281  ACCACCGCTACCAGCGGTGGTTTGTTTGCCGGATCAAGAGCTACCAACTCTTTTTCCGAA
2341  GGTAACTGGCTTCAGCAGAGCGCAGATACCAAATACTGTCCTTCTAGTGTAGCCGTAGTT
2401  AGGCCACCACTTCAAGAACTCTGTAGCACCGCCTACATACCTCGCTCTGCTAATCCTGTT
2461  ACCAGTGGCTGCTGCCAGTGGCGATAAGTCGTGTCTTACCGGGTTGGACTCAAGACGATA
2521  GTTACCGGATAAGGCGCAGCGGTCGGGCTGAACGGGGGTTCGTGCACACAGCCCAGCTT
2581  GGAGCGAACGACCTACACCGAACTGAGATACCTACAGCGTGAGCTATGAGAAAGCGCCAC
2641  GCTTCCCGAAGGGAGAAGGCGGACAGGTATCCGGTAAGCGGCAGGGTCGGAACAGGAGA
2701  GCGCACGAGGGAGCTTCCAGGGGAAACGCCTGGTATCTTTATAGTCCTGTCGGGTTTCG
2761  CCACCTCTGACTTGAGCCGTCGATTTGTGATGCTCGTCAGGGGGCGGAGCCTATGGAA
2821  AAACGCCAGCAACGCGGCCTTTCCCTGATTCTGTGGATAACCGTATTACCGCCTTTGAGTGAGC
2881  GTTCTTTCCTGCGTTATCCCCTGATTCTGTGGATAACCGTATTACCGCCTTTGAGTGAGC
2941  TGATACCGCTCGCCGCAGCCGAACGACCGAGCGCAGCGAGTCAGTGCGCTCACACCGCATATG
3001  AGAGCGCCTGATGCGGTATTTTCTCCTTACGCATCTGTGCGGTATTTCACACCGCATATG
3061  GTGCACTCTCAGTACAATCTGCTCTGATGGCCGCATAGTTAAGCCAGTATACACTCCGCTA
3121  TCGCTACGTGACTGGGTCATGCTGTCCCCGGCATCCGCTTACAGACAAGCTGTGACCGTCTCCGGAGC
3181  TGACGGGCTTGTCTGCTCCCGGCATCCGCTTACAGACAAGCTGTGACCGTCTCCGGAGC
3242  TGCATGTGTCAGAGGTTTCACCGTCATCACCGAAACGCGCGAGGCAGCTGCGGTAAAGC
3301  TCATCAGCCGTGGTCGTGAAGCGATTCACAGATGTCTGCTCTGATAAAGCGGGCATGTGTTAAGGCCG
3361  TTGAGTTTCTCCAGAAGCGTTAATGTCTGGCTTCTGATAAGCGGGCATGTGTTAAGGGCG
3421  GTTTTTTCCTGTTTGGTCACTTGATGCCTCCGTGTAAGGGGGAATTTCTGTTCATGGGGG
```

FIG. 3C

```
3481  TAATGATACCGATGAAACGAGAGAGGATGCTCACGATACGGGTTACTGATGATGAACATG
3541  CCCGGTTACTGGAACGTTGTGAGGGTAAACAACTGGCGGGTATGGATGCGGCGGGACCAGA
3601  GAAAAATCACTCAGGGTCAATGCCAGCGCTTCGTTAATACAGATGTAGGTGTTCCACAGG
3661  GTAGCCAGCAGCATCCTGCGATGCAGATCCGAACATAATGTGCAGGCGCTGACTTCC
3721  GCGTTTCCAGACTTTACGAACACGGAAACCGAAGACCATTCATGTTGTTGCTCAGGTCG
3781  CAGACGTTTTGCAGCAGCAGTCGCTTCACGTTCGCTCGGTATCGGTGATTCATTCTGCT
3841  AACCAGTAAGGCAACCCCGCCAGCTTAGCCCGGTTCCTCAACGACAGGAGCACGATCATGC
3901  GCACCCGTGGCCAGACCCAACGCTGCCCGAGATGCGCCGTGCCGCTGCTGGAGATGG
3961  CGGACGCGATGGATATGTTCTGCCAAGGTTGGTTTGCGCATTCACAGTTCTCCGCAAGA
4021  ATTGATTGGCTCCAATTCTTGGAGTGGTGAATCCGTTAGCGAGGTGCCGCCGGCTTCCAT
4081  TCAGGTCGAGGTGGCCCGCTACAATCCATGCCAACCCGTTCCATGTGCTCGCCGAGGCAGACAAGTA
4141  TAGGGCGCGCCTACAATCAGCGCGGTCCAGTGATCGAAGTTAGGCTGGTTAAGAGCCGGAGCGATCC
4201  CGCCGTGACGATCAGCGCGGTCCAGTGATCGAAGTTAGGCTGGTTAAGAGCCGGAGCGATCC
4261  TTGAAGCTGTCCCTGATGGTCGTCGTAGTGCCGGAAGCGAGAAGAATCATAATGGGGAAGGCCATCCAGCCTCGCGT
4321  CATCCCGATGCCCGCCGGAAGCGAGAAGAATCATAATGGGGAAGGCCATCCAGCCTCGCGT
4381  CGCGAACGCCAGAAGACGTAGCCAGGACCTAGCCATGCGCGTCGGCCGCATGCCGGCGATAATGGCCTG
4441  CTTCTCGCCGAAACGTTTGGTGGCGGACCAGTGACATCGTCGCGCTTGAGCGAGGGCGTGCAA
4501  GATTCCGAATACCGCAAGCGACCAGCCGATCATCGTCGCGCTTGAGCGAGGGCGTGCAA
4561  GCCGAAAATGACCCAGAGCGCTGCCGGCACCTGTCCTACGAGTTGCATGATAAAGAAGAC
4621  AGTCATAAGTGCGGCGACGATAGTCATGCCGTCGACTCGGTCGACTCCTGCATTAGGAAGCA
4681  GAAGGCTCTCAAGGCATCGGTCGGCCGTTGAGCACCGCAAGGAATGGTGCATGCAAGGA
4741  GCCCAGTAGTAGGTTGAGGCCGTTGAGCACCGCAAGGAATGGTGCATGCAAGGA
4801  GATGGCGCCCAACAGTCCCCGGCCGAGCCCGATCTTCCCCATCGGTGATGTCGGCGATATAGGC
4861  GCTCATGAGCCGAAGTGGCGAGCCCGATCTTCCCCATCGGTGATGTCGGCGATATAGGC
4921  GCCAGCAACCGCCACCTGTGCCGCCGCCGGTGATGCGTCCGGCGTAGAGGAT
4981  CCGGAGCTTATGCTGTGCACTGACTGCAGTGCACCAATGCTTCTGGCGTCAGGCAGCCATCGGAAGC
5041  TGTGGTATGCGTGTGCAGTCGTAAATCACTGCATAATTCGTCGTCGCTCAAGGCGCACTC
5101  CCGTTCTGGATAATGTTTTTTGCGCCGACATCATAACGGTTCTGCCAAATATTCTGAAAT
5161  GAGCTGTTGACAATTAATCATCGGCTCGTATAATGTGTGGAATTGTGAGCGGATAACAAT
5221  TTCACACAGGAAACAGAA    5238
```

FIG. 4A

```
   1  GCGCCCAATACGCAAACCGCCTCTCCCCGGCGTTGGCCGATTCATTAATGCAGCTGGCA
  61  CGACAGGTTTCCCGACTGGACCCCAGGCTTTACACTTTATGCTTCCGGCTTCCGTATGTTGTGGAAT
 121  CACTCATTAGGCACCCCAGGCTTTACACAGGAAACAGCTATGACCATGATTACGAATTCCCGG
 181  TGTGAGCGGATAACAATTCACACAGGAAACAGCTATGACCATGATTACGAATTCCCGG
 241  AAGTTCAAGGTGTGGAGTCTGGAGTTCACTTTCAGTGACTATTACATGTATTGGGTTCCCTGAAACTCT
 301  CCTGTGCAGCCTCTGGATTCACTTTCAGTGACTATTACATGTATTGGGTTCGCCAGACTC
 361  CGGAAAAGAGGCTGGAGTGGTCGCAACCATTAGTGATGGTGGTAGTTACACCTACTATC
 421  CAGACAGTGTGAAGGGGCGATTCACCATCTCCAGAGACAATGCCAAGAACAACCTGTACC
 481  TGCAAATGAGCAGTCTGAAGTCTGATGACACAGCCATGTATTACTGTGCAAGAGATAAGG
 541  CCTACTATGGTAACTACGGCGATGCTATGGACTACTGGGGTCAAGGAACCTCAGTCACCG
 601  TCTCCTCAGCCAAAACGACACCCCCATCTGTCTATCCACTGGCCCCTGGATCTGCTGCCC
 661  AAAACTAACTCCATGTGACCCTGGAATCCCTGTGTTGCACACCTTCCCCAGCTGTCCTGC
 721  CAGTGACCTGGAACTCTGGAATCCCTGTGTTGCACACCTTCCCCAGCTGTCCTGC
 781  AGTCTGACCTCTACACTCTGAGCAGTGTGCCCAGCAGCAAGTGGACACTGGCCTGGACG
 841  AGACCGTCACCTGCAACGTTGATCAGTGCCACCCGGCGTTACCCAACTTAATCGCCTTGCAGCACATG
 901  TGCCCAGGGATTGTGTGACTGGGAAAAACCCGGCGTTACCCAACTTAATCGCCTTGCAGCACATC
 961  TACAACGTCGTGACCAGCTGGCTGGCTAATAGCCGAAGAGGCCCACCACCTTCCCAACAGT
1021  CCCCTTTCGCCCAGCTGAATGGCGCTGAATGGCGCCTGATGCGTATTTCTCCTTACGCATCTGTGCG
1081  TGCGCAGCCTGAATGGCGCTGAATGGCGCCTGATGCGTATTTCTCCTTACGCATCTGTGCG
1141  GTATTTCACACCGCATATGGTCCACTCTCAGTACAATCTGCTCTGATGCCGCATAGTTAA
1201  GCCAGCCCCGACACCCGCCAACACTGTGACCGTCTCCGGGGAGCTGCATGTGTCAGAGGTTTCAC
1261  CATCCGCTTACAGACAAGCTGTGACCGTCTCCGGGGAGCTGCATGTGTCAGAGGTTTCAC
1321  CGTCATCACCGAAAAGCGCGAGACGAAAAAGGGCCTCGTGATACGCCTATTTTTATAGGTTA
1381  ATGTCATGATAATAATGGTTTCTTAGAGCGTCAGGTGGCACTTTTCGGGGAAATGTGCGCG
1441  GAACCCTATTTGTTTATTTTCTAAATACATTCAAATATGTATCCGCTCATGAGACAAT
1501  AACCCTGATAAATGCTTCAATAATATTGAAAAAGGAAGAGTATGAGTATTCAACATTTCC
1561  GTGTCGCCCTTATTCCCTTTTTTGCGCATTTGCCTTCGTGCACCCAGAAA
1621  CGCTGGTGAAAGTAAAAGATGCTGAAGATCAGTTGGGTGCACGAGTGGGTTACATCGAAC
1681  TGGATCTCAACAGCGGTAAGATCCTTGAGAGTTTTCGCCCCGAAGAACGTTTTCCAATGA
```

FIG. 4B

```
1741  TGAGCACTTTTAAAGTTCTGCTATGTGGCGCGGGTATTATCCGTATTGACGCCGGGCAAG
1801  AGCAACTCGGTCGCCGCATACACTATTCTCAGAATGACTTGGTTGAGTACTCACCAGTCA
1861  CAGAAAAGCATCTTACGGATGGCATGACAGTAAGAGAATTATGCAGTGCTGCCATAACCA
1921  TGAGTGATAACACTGCGGCCAACTTACTTCTGACAACGATCGGAGGACCGAAGGAGCTAA
1981  CCGCTTTTTGCACAACATGGGGGATCATGTAACTCGCCTTGATCGTGTTGGGAACCGGAGC
2041  TGAATGAAGCCATACCAAACGACGAGCGTGACACCACGATGCCTGTAGCAATGGCAACAA
2101  CGTTGCGCAAACTATTAACTGGCGAACTACTTACTTCTAGCTTCCCGGCAACAATTAATAG
2161  ACTGGATGGAGGCGGATAAAGTTGCAGGACCACTTCTGCGCTCGGCCCTTCCGGCTGGCT
2221  GGTTTATTGCTGATAAATCTGGAAGCCCGGTGAGCGTGGTATCGTAGTTATCTACACGAC
2281  TGGGCCAGATGGTAAGCCCTCCCGTAGTTATCGTAGTATAGGTGCCTCACTGATTAAGCATTGGT
2341  CTATGGATGAACGAAATAGACAGATCGCTGAGATAGGTGCCTCACTGATTAAGCATTTTAAT
2401  AACTGTCAGACCAAGTTACTCATATATACTTTAGATTAAACTTCATTTTAAT
2461  TTAAAAGGATCTAGGTGAAGATCCTTTTGATAATCTCATGACCAAATCCCTTAACGTG
2521  AGTTTTCGTTCCACTGAGCGTCAGATCTGTTCGCCTTGCTTCTTGAGATC
2581  CTTTTTTTTCTGCGCGTAATCTGCTGCTTGCAAACAAAAAACCACCGCTACCAGCGGTGG
2641  TTTGTTTGCCGGATCAAGAGCTACCAACTCTTTTTCCGAAGGTAACTGGCTTCAGCAGAG
2701  CGCAGATACCAAATACTGTCCTTCTAGTGTAGCCGTAGTTAGGCCACCACTTCAAGAACT
2761  CTGTAGCACCGCCTACATACCCTCGCTCTGCTAATCCTGTTACCAGTGGCTGCTGCCAGTG
2821  GCGATAAGTCGTGTCTTACCGGGTTGGACTCAAGACGATAGTTACCGGATAAGGCGCAGC
2881  GGTCGGGCTGAACGGGGGTTCGTGCACACAGCCCAGCTTGGAGCGAACGACCTACACCG
2941  AACTGAGATACCTACAGCGTGAGCTATGAGAAAGCGCCACGCTTCCCGAAGGGAGAAAGG
3001  CGGACAGGTATCCGGTAAGCGGCAGGGTCGGAACAGAGAGCGCACGAGGGAGCTTCCAG
3061  GGGAAACGCCTGGTATCTTTATAGTCCTGTCGGGTTTCGCCACCTCTGACTTGAGCGTC
3121  GATTTTTGTGATGCTCGTCAGGGGGGCGGAGCCTATGGAAAAACGCCAGCAACGCGGCCT
3181  TTTTACGGTTCCTGGCCTTTTGCTGGCCTTTTGCTCACATGTTCTTTCCTGCGTTATCCC
3242  CTGATTCTGTGGATAACCGTATTACCGCCTTTGAGTGAGCTGATACCGCTCGCCGCAGCC
3301  GAACGACCGAGCGCAGCGAGTCAGTGAGCGAGGAAGCGGAAGA    3343
```

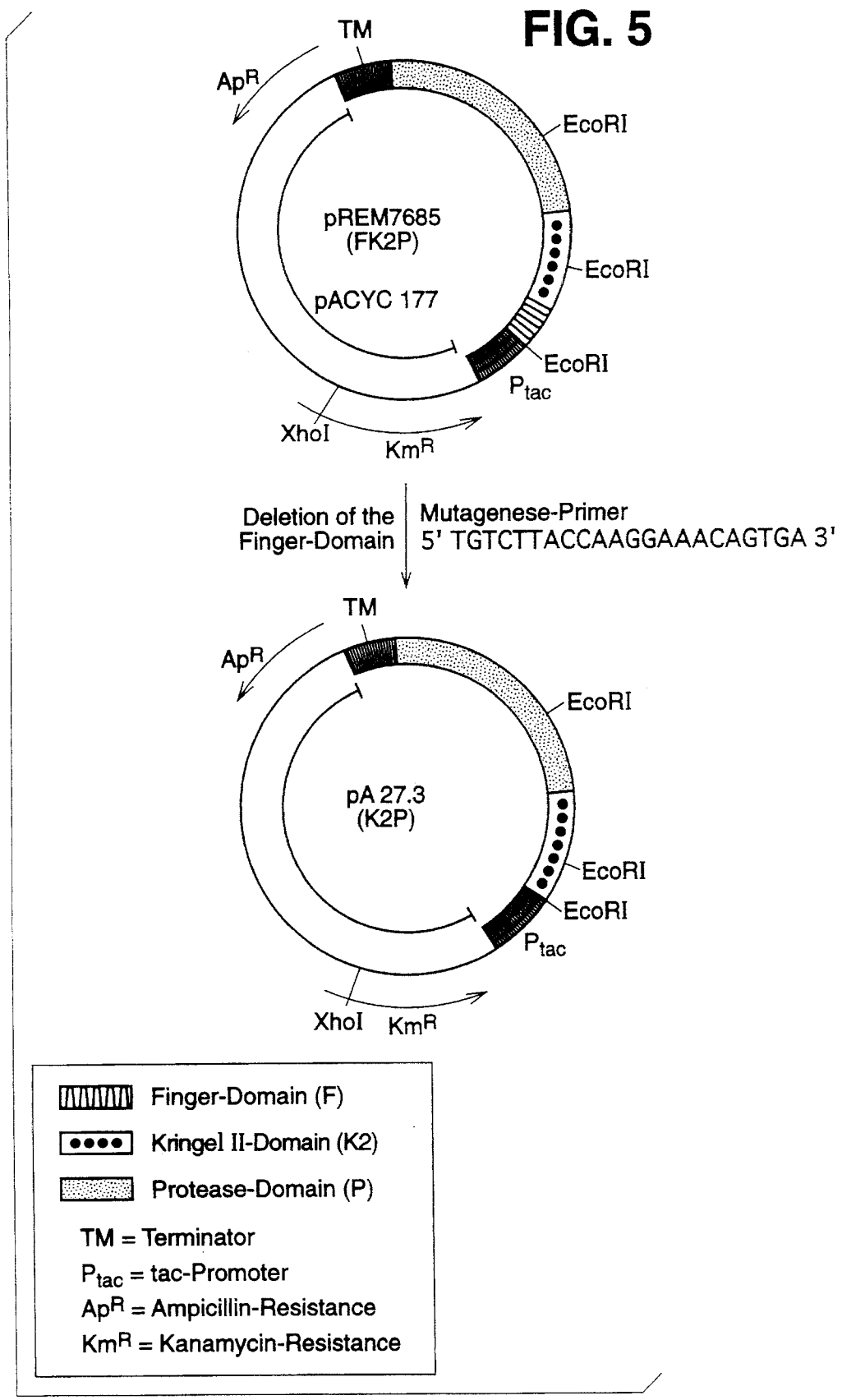

1

PROCESS FOR THE ACTIVATION OF T-PA OR ING AFTER GENETIC EXPRESSION IN PROKARYOTES

This application is a continuation of application Ser. No. 07/942,370 filed Sep. 9, 1992; now abandoned, which is a continuation of application Ser. No. 07/498,500 filed Mar. 23, 1990, now abandoned; which is a continuation-in-part of application Ser. No. 07/076,207, as PCT/EP86/00610, Oct. 23, 1986, now abandoned.

SUMMARY OF THE INVENTION

The invention concerns an oxidative process for activation of the stimulability of eukaryotic protein including interpheron tPA and IgC containing disulphide bridges after expression in prokaryotes by recombinant genetic technology.

BACKGROUND

The invention concerns a process for the activation of gene-technologically produced, disulphide bridge-containing eukaryotic proteins after expression in prokaryotes using recombinant genetic techniques.

In the case of the expression of heterologous proteins in prokaryotes, in the host cells these proteins often form inactive, sparingly soluble aggregates (so-called "refractile bodies") which, in addition, are also contaminated with proteins of the host cells. It is assumed that the formation of such "refractile bodies" is a result of the high protein concentrations in the cell arising in the case of the expression. It is known that, in the case of the formation of large amounts of enzymes in the cell, the aggregation of the enzymes to insoluble, high molecular, mostly inactive particles takes place. Before such proteins can be used, e.g. for therapeutic purposes, they must consequently be purified and converted into their active form.

According to known processes, a reactivation of such proteins present as aggregates takes place in several steps (cf. e.g. R. Jaenicke, FEBS Federation of European Biochemical Societies, Vol. 52 (1979) 187 to 198; R. Rudolph et al., Biochemistry 18 (1979) 5572 to 5575).

In the first step, a solubilisation is achieved by the addition of strong denaturing agents, for example guanidine hydrochloride or urea, in high concentration or by the addition of strongly acidic agents, for example glycine/phosphoric acid mixtures. As further adjuvants, there have proved useful reducing SH reagents (e.g. dithioerythritol, DTE) and EDTA, for example in the renaturing of LDH (lactic dehydrogenase). Insofar as the protein is contaminated by proteins of the host cells, as next step there follows a purification with per se known and usual methods, e.g. gel or ion exchanger chromatography. Subsequently, it is highly diluted in order that the concentration of the denaturing agent becomes smaller. In the case of the use of guanidine hydrochloride, it is thereby diluted to values below 0.5 mole/l. In the case of enzymes with free SH groups, the addition of agents protecting the SH groups proves to be advantageous (cf. e.g. R. Jaenicke, Journal Polymer Science, Part C, 16 (1967) 2143 to 2160).

In EP-A-0114506, processes are described for the isolation, purification and reactivation of some heterologous expression products from bacterial cultures; for the reactivation, the solutions of the "refractile bodies" in a strong denaturing agent are a) transferred directly into a solution of a weaker denaturing agent which is then subjected to oxidising conditions for the reformation of disulphide bridges; b) the protein is sulphonated, then transferred into a solution in a weak denaturing agent and the S-sulphonate groups are converted into —S—S— group by treatment with a sulphhydryl reagent in its reduced and oxidised from, e.g. with GSH/GSSG; or c) the solution in a weak denaturing agent is treated directly with the sulphhydryl reagent, e.g. with GSH/GSSG. A typical example in which the above-discussed problems arises is t-PA.

The main component of the protein matrix of coagulated blood is polymeric fibrin. This protein matrix is dissolved by plasmin which is formed from plasminogen via activation by the so-called plasminogen activators, e.g. by t-PA (tissue-type plasminogen activator). The enzymatic activity of natural t-PA or of t-PA obtained gene-technologically from eukaryotes (catalytic activation of plasminogen to plasmin) is very low in the absence of fibrin or fibrin cleavage products (FCP) but can be substantially increased in the presence of these stimulators (by more then a factor of 10). This so-called stimulatability of the activity is a decisive advantage of t-PA in comparison with other known plasminogen activators, such as urokinase or streptokinase (cf. e.g. M. Hoylaerts et al., J. Biol. Chem., 257 (1982) 2912 to 2919; Nieuwenhiuzen et el., Biochemics et Biophysica Acta 755 (1983) 531 to 533). Therefore, the factor of the stimulatability with BrCN cleavage products is variously given in the literature and given a value of up to 35.

A t-PA-like, non-glycosilated product is also formed in genetically manipulated prokaryotes (after introduction of the c-DNA); however, such a product does not have the stimulatability of the activity of a t-PA from eukaryotes. It is conceivable that the reason for this is that the redox conditions in the prokaryote cell differ in such a way from eukaryote cells from which the gene originates that, ab initio, a non-active product is formed which, for example, could be due to the fact that numerous SS bridges which the natural active molecule contains are linked in a false way or are not even formed. However, for the therapeutic use of t-PA, there is necessary not only the enzymatic activity as such but, in addition, also its stimulatability. Regarding the fact that the prokaryote cells presumably do not provide the correct conditions in order to form the activity of eukaryotic proteins in the correct way, reference is made to other substances in the EMBO Journal 4, No.3 (1985) 775 to 780.

According to EPO 093619, for the reactivation of t-PA, the cell pellets obtained from *E. coil* are suspended in 6 mole/l. guanidine hydrochloride, treated with ultrasonics, incubated and subsequently dialysed for four hours against a solution of tris-HCl (pH=8.0), sodium chloride, EDTA and Tween 80. After dialysis, it is centrifuged, whereby the plasminogen activator activity is to be found in the supernatant. t-PA renatured in this way is admittedly proteolytically active but shows no measureable stimulatability by BrCN cleavage products (BrCN-FCP) of fibrin according to the process described in J. H. Vereijen, Thromb. Haemostas., 48 (3), 260–269 (1982).

For the reactivation of denatured proteins, no generally useable process is known from the state of the art; this applies quite especially for t-PA because the native protein possesses a very complex structure; it contains a free thiol group and 17 SS bridges which theoretically can be linked in $2.2 \times 10^{20}$ different ways, whereby only one structure corresponds to the native state. The processes known from the state of the art for the reactivation of t-PA admittedly lead to a proteolytically active t-PA but which shows no measurable stimulatability; an activation process which leads to stimulatable t-PA is not known.

BRIEF DESCRIPTION OF THE DRAWINGS

FIGS. 3A–3C list the nucleotide sequence of expression plasmid pBT111.

FIGS. 4A and 4B list the nucleotide sequence of expression plasmid p10169.

FIG. 5 shows the construction of plasmid pA27.3 from plasmid pREM7685.

DETAILED DESCRIPTION

Figure 1:
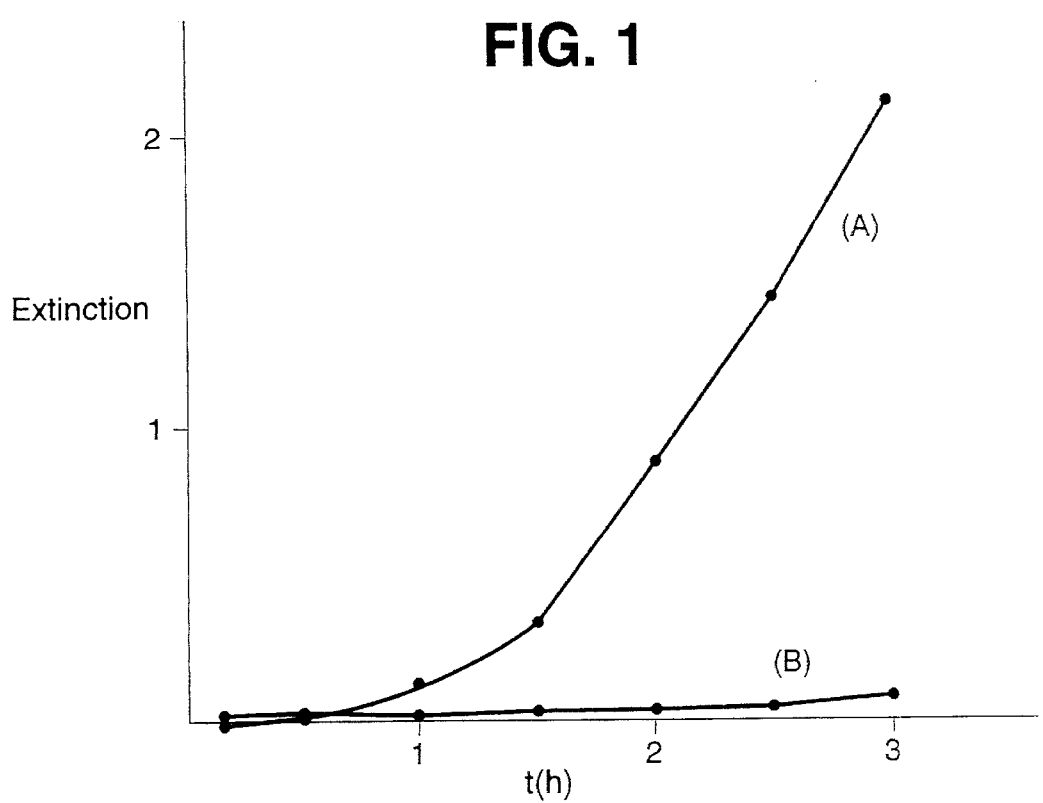
FIG. 1 shows, in line A, the activity of TPA in the presence of CNBr-FCP in a standard assay and in line B, the activity of TPA in the absence of CNBr-FCP.

Therefore, it is the task of the present invention to make available a process for the complete activation of gene-technologically produced, heterologous, disulphide bridge-containing eukaryotic proteins after expression in prokaryotes; this task is solved with the subject of the present invention.

The subject of the invention is a process for the activation of gene-technologically produced, heterologous, disulphide bridge-containing eukaryotic proteins after expression in prokaryotes according to patent claim 1 by cell digestion, solubilisation under denaturing and reducing conditions and activation (renaturing) under oxidising conditions in the presence of GSG/GSSG, which is characterised in that, in the step of the activation, one works at a pH value of 9 to 12, a GSH concentration of 0.1 to 20 mmole/l., a GSSG concentration of 0.01 to 3 mmole/l. and with a non-denaturing concentration of the denaturing agent.

Preferred embodiments of this process are the subject of the subsidiary claims.

As denaturing agent, there can, as a rule, be used a denaturing agent usually employed for activation under oxidising conditions or arginine; amongst the known denaturing agents, there is preferred guanidine hydrochloride or urea or its derivatives of the general formula $R_2$—CO—$NRR_1$ (I) wherein R and $R_1$ are H or alkyl with 1 to 4 carbon atoms and $R_2$ is H or $NHR_1$ or alkyl with 1 to 3 carbon atoms. Furthermore, arginine has proved to be useful. Furthermore, mixtures of these denaturing agents can be used. This activation step is preferably also carried out in the presence of a foreign protein; as such, there is, as a rule, suitable any foreign protein, so long as it is not proteolytically active; bovine serum albumin (BSA) is preferably used, e.g. in an amount of 1 to 3 mg./ml. The addition of BSA brings about a slight increase of the yield and stabilisation of the protein (probably by protection against surface denaturing and/or proteolytic breakdown.

The other process conditions can correspond to the known and usual conditions for the reactivation steps from the prior art. The period of the activation (incubation) preferably amounts to 20 to 48 hours at room temperature. The half life time of the activation lies, in the presence of 0.5 mmole/l. reduced (GSH) and oxidised (GSSG) glutathione, at about 10 to 15 hours at 20° C. In the case of a longer incubation (48 hours) under reoxidation conditions, as a rule the stimulatability by CNBr-FCP decreases. The activation step is preferably carried out in the presence of EDTA, whereby the most expedient concentration amounts to about 1 mmole/l. EDTA.

The process steps preceding and following the activation step (reoxidation/activation), such as cell digestion, solubilisation (solubilisation/reduction) and possibly one or more of the purification operations preceding and/or following the activation step, can be carried out according to known and usual methods for such processes from the prior art, e.g. from EP-A 0114506 and EP-A-0093619; however, for a result which is optimal with regard to yield and activations, it can be expedient to carry out individual or all process steps having regard to one or more of the heredescribed process embodiments. In particular, it is also possible to carry out the step of activation according to the invention in the mixture obtained after digestion without previous denaturing and/or reduction but with lower yield. The expression is carried out in prokaryotes, preferably in *P. putida* and especially in *E. coli*. However, the process according to the invention is just as suitable when one expresses in other prokaryotes (e.g. Bacilli).

The cell digestion can be carried out by methods usual herefor, e.g. by means of ultrasonics, high pressure dispersion or lysozyme; it is preferably carried out in a buffer solution suitable for the adjustment of a neutral to weakly acidic pH value as suspension medium, such as e.g. in 0.1 mole/l. tris HCl. After the cell digestion, the insoluble components ("refractile bodies") are separated off in any desired way, preferably by centrifuging off at comparatively high g values and comparatively long contrifuging times or by filtration. After washing with agents which do not disturb t-PA but possibly dissolve foreign proteins, e.g. water, phosphate buffer solution, possibly with the addition of mild detergents, such as Triton,, the precipitate (pellet) is subjected to the solubilisation (solubilisation/reduction). The solubilisation preferably takes place in the alkaline pH range, especially at pH=8.6 ±0.4 and in the presence of a reducing agent of the mercaptan group and of a denaturing agent.

As denaturing agent, there can be used the denaturing agents known and usual from the state of the art, e.g. from EP-A-0114506, and especially guanidine hydrochloride or urea. The concentration of guanidine hydrochloride expediently amounts to about 6 mole/l., that of urea to about 8 mole/l. Compounds of the general formula I can also be used.

As reducing agent for the mercapto group, there can be used e.g. reduced glutatione (GSH) or 2-mercaptoethanol, e.g. in a concentration of about 50 to 400 mmole/l. and/or especially DTE (dithioerythritol) or DTT (dithiothreitol), e.g. in a concentration of about 80 to 400 mmole/l. The solubilisation expediently takes place at room temperature over a period (incubation) of 1 to several hours, preferably of two hours. For the prevention of oxidation of the reducing agent by atmospheric oxygen, it can be expedient to add EDTA. Besides the solubilising/reduction, the solubilising step also has a purification effect since a large part of material (foreign proteins) not cross-reacting immunologically with t-PA goes into solution.

After the solubilisation and before the activation step, per se known and usual purification steps can be introduced; as purification methods, there come into question, e.g.. steric exclusion chromatography (SEC)(in the presence of guanidine hydrochloride or urea) or ion exchangers (in the presence of urea or its derivatives); a non-specific reoxidation can be prevented by addition of a reducing agent (e.g. 2-mercaptoethanol) or by pH value 4.5 (cf. e.g. R. Rudolph, Biochem. Soc. Transactions, 13 (1985) 308 to 311). If DTE was used in the preceding solubilisation step, this must be separated off in the purification step. The purification can take place e.g. by SEC over Sephadex G 100 in the presence of guanidine hydrochloride and of a reducing agent, e.g. of GSH, at a pH of 1 to 4 (in this step, a large amount of foreign protein can be separated off); or by separating off of the denaturing/reducing agent by desalination over Sephadex G 25 in 0.01 mole/l. HCl or 0.1 mole/l. acetic acid. Alternatively, the separating off of the denaturing/reducing agent is possible by dialysis against the same solutions.

A further purification step can follow the reactivation step; such a purification takes place by means of dialysis of also a subsequent isolation of the activated tPA, for example by affinity chromatography, for example over Lys-Sepharose.

Another embodimental form of the invention depends upon the formation of the mixed disulphides of gene-technologically produced, heterologous, disulphide bridge-containing eukaryotic proteins and glutathione (in the following abbreviated t-PASSG). This can simplify not only the separation of foreign proteins in the denatured state but also the further purification of the native protein. A purification after modification of the thiol groups has the advantage that the protein is protected against air oxidation and thus is stable in a greater pH range and a change of the net charging simplifies the purification. In particular, a separation from non-modified protein can advantageously be carried out by ion exchanger treatment.

For the formation of the mixed disulphides, the dialysed, reduced protein, purified from denaturing and reducing agents, was incubated with a diluted, 0.2 mole/l., solution of GSSG containing a denaturing agent. The activation took place after separation off of the denaturing and oxidation agent at a pH value of 7 to 10.5, at a GSH concentration of 0.5 to 5 mmole/l. and with a non-denaturing concentration of the denaturing agent.

In all other reaction steps, the activation of the protein via the formation of mixed disulphides with GSSG corresponds to the embodimental forms for the activation of the previously mentioned part of the invention. In the case of this embodimental form, the pH optimum lies at 8.5, the yield is about twice as high and the activated protein is stable in the regeneration buffer over a longer time.

According to the invention, it is possible so to activate t-PA from prokaryotes that there is achieved not only an activation of the normal biological activity but, in addition, a stimulatability in the above-defined sense is achieved which far excess the stimulatability of the native t-PA and is greater than a factor of 10 and can even exceed a factor of 50.

A further eukaryotic protein which, according to the invention, can be activated after expression in prokaryotes is β-interferon.

The following Examples further explain the invention without limiting it thereto. If not stated otherwise, statements of percentage refer to percent by weight and statements of temperature to degrees Celsius.

EXAMPLE 1 a) Preparation of the "Refractile Bodies"

100 g. E. coli moist cell mass, taken up in 1.5 l. of 0.1 mole/l. tris-HCl (pH 6.5) and 20 mmole/l. of EDTA were homogenised (Ultra-Turrax, 10 sec.) and 0.25 mg./ml. lysozme added thereto. After 30 min. incubation at room temperature, it was again homogenised and cooled to 3° C. The cell digestion was achieved by high pressure dispersion (500 kg./cm²). Subsequently, it was after-rinsed with 300 ml. of 0.1 mole/l. tris/HCl (pH 6.5) and 20 mmole/l. EDTA. After centrifuging (2 hrs at 27000 g, 4° C.), the pellet was taken up in 1.3 l. of 0.1 mole/l. tris/HCl (pH 6.5), 20 mmole/l. EDTA and 2.5% Triton X-100 and homogenised. After renewed centrifuging (30 min. at 27000 g, 4° C.), the pellet was taken up in 1.3 l. of 0.1 mole/l. tris/HCl (pH 6.5), 20 mmole/l. EDTA and 0.5% Triton X-100 and homogenised. Alternatingly centrifuging (30 min at at 27000 g, 4° C.) and homogenisation of the pellets in 1 l. of 0.1 mole/l. tris/HCl (pH 6.5) and 20 mmole/l. EDTA was further carried out three times.

The t-PA content of the "refractile bodies" preparations was quantified by the SDS-PAGE, identification of the t-PA bands by "Western blotting" and densitometric analysis. In the case of the SDS-PAGE and "Western blotting", the "refractile bodies" show a strong t-PA band with a molecular weight of about 60 kDa. The t-PA proportion of the total protein content of the "refractile bodies" amounts to about 21%.

b) Solubilising/reduction of the "Refractile Bodies"

"Refractile bodies" were incubated at a protein concentration of 1 to 5 mg./ml. in 0.1 mole/l. of tris/HCl (pH 8.6), 6 mole/l. guanidine hydrochloride, 0.15 to 0.4 mole/l. DTE and 1 mmole/l. EDTA for 2 to 3 hrs. at room temperature. Thereafter, insoluble material (cell wall fragments etc.) was centrifuged off (e.g. 30 min at 35000 to 50000 g, 4° C.) The pH of the supernatant was adjusted with conc. HCl to pH 3. Denaturing and reducing agents were separated off by dialysis against 0.01 mole/l. HCl at 4° C.

c) Reoxidation/activation

Reoxidation/activation took place by means of a 1:50 to 1:200 dilution in 0.1 mole/l. tris/HCl (pH 10.5), 1 mmole/l. EDTA, 1 mg./ml. BSA, 0.5 mole/l. L-arginine, 2 mmole/l. GSH, 0.2 mmole/l. GSSG. After 17 to 24 hours activation at about 30° C., there was determined the activity and the yield in comparison with the activity of native glycosilated t-PA from eukaryonts.

Yield referred to the total protein content of the "refractile bodies": 2.5 +/−0.5% stimulatability: 10 +/−5.

Yield referred to the t-PA portion of the "refractile bodies": about 12%.

d) Reoxidation/activation Without Separation of the Denaturing/reducing Agent

"Refractile bodies" were incubated at room temperature at a protein concentration of 1.25 mg./ml. in 0.1 mole/l. tris/HCl (pH 8.6), 6 mole/l. guanidine hydrochloride, 0.2 mole/l. DTE and 1 mmole/l. EDTA for 2 hours at room temperature. Thereafter, reoxidation was immediately initiated by a 1:100 dilution in 0.1 mole/l. tris/HCl (pH 10.5), 1 mmole/l. EDTA, 1 mg./ml. BSA, 0.3 mole/l. L-arginine and the amounts of GSSG given in the Table. In addition, in the activation batch was present a residual concentration of 0.06 mole/l. guanidine hydrochloride and 2 mmole/l. DTE.

| GSSG (mmole/l.) | yield' (%) | stimulatability (factor) |
| --- | --- | --- |
| 0.2 | 0 | — |
| 1 | 0.13 | 4.0 |
| 5 | 1.49 | 7.4 |

-continued

| GSSG (mmole/l.) | yield' (%) | stimulatability (factor) |
|---|---|---|
| 6 | 1.28 | 5.4 |
| 7 | 1.04 | 5.8 |
| 9 | 0.98 | 5.2 |
| 10 | 1.77 | 10.0 |
| 15 | 0 | — |
| 20 | 0 | — |

' = yield of active t-PA, referred to the total protein content of the "refractile bodies".

EXAMPLE 2

An RB ("refractile bodies") preparation (about 5 mg.) was incubated for 2 to 3 hours at room temperature in 1 ml. of 0.1 mole/l. tris/HCl (pH=8.6), 6 mole/l. guanidine hydrochloride and 0.15–0.2 mole/l. DTE. Insoluble material (cell wall fragments etc.) were thereafter separated off by centrifuging (20 minutes at 17000 g). Denaturing and reducing agents were removed by gel filtration over Sephadex G 25 (superfine) in 0.01 mole/l. HCl. The sample was thereby diluted by about the factor 5 to 10. The reduced material was stored at −20° C. in 0.01 mole/l. HCl.

EXAMPLE 3

In the following Tables is summarised the influence of various parameters according to the invention on the activation and stimulatability. For these reoxidation experiments, the solubilised, reduced protein according to Example 2 was not further prepurified.

The reduced protein (in 0.01 mole/l. HCl) was activated by dilution of 1:10 to 1:500 in "reoxidation buffer". The activation was determined at room temperature after 22 to 48 hours incubation. The activity of the reoxidised protein refers to a "standard reoxidation" (=100%) in:

0.1 mole/l. tris/HCl (pH=10.5)+L mmole/l. EDTA

+0.5 mole/l. L-arginine

+1 mg./ml. BSA

+0.5 mmole/l. GSH (reduced glutathione)

+0.5 mmole/l. GSSG (glutathione disulphide).

The stimulatability is calculated from $$\Delta E_{+CNBr\ FCP}/\Delta E_{-CNBr\ FCP}$$

(cf. W. Nieuwenhuizen et al., Biochemica et Biophysica Acta 755 (1983) 531 to 533). The activity (in percent) and the stimulatability (factor) was determined according to J. H. Verheijen Thromb. Haemostas. 48 (3), 266–269 (1982).

The following results were obtained:

1. Dependency of the activation yield upon the addition of L-arginine or guanidine hydrochloride.
   Reoxidation in 0.1 mole/l. tris/HCl (pH 10.5)
   +1 mmole/l. EDTA
   +1 mg./ml. BSA
   +0.5 mmole/l. GSH
   +0.5 mmole/l. GSSG
a) L-arginine

| L-arginine (mole/l.) | activity (%) | stimulatability (factor) |
|---|---|---|
| 0 | 4 | 2.5 |
| 0.25 | 98 | 7.5 |
| 0.5 | 100 | 21.9 |
| 0.75 | 27 | 16.3 |
| 1.0 | 23 | 3.5 |

In the case of this experiment, it is to be borne in mind that t-PA is inhibited by L-arginine. The drop of the activity yield at higher L-arginine concentrations is, therefore, to be corrected with regard to the inhibition.

b) Guanidine hydrochloride (Gdn/HCl)

| Gdn/HCl (mole/l.) | activity (%) |
|---|---|
| 0 | 11 |
| 0.25 | 22 |
| 0.5 | 53 |
| 0.75 | 58 |
| 1.0 | 12 |

2. Dependency of the activation yield upon the addition of urea and urea derivatives.

Reoxidation in 0.1 mole/l. tris (pH 10.5), 1 mmole/l. EDTA, 1 mg./ml. BSA, 5 mmole/l. GSH, 0.2 mmole/l. GSSG

| a) Urea | |
|---|---|
| urea. (mole/l.) | activity (%) |
| 0 | 1 |
| 0.5 | 20 |
| 1 | 59 |
| 1.5 | 126 |
| 2 | 162 |
| 2.5 | 141 |
| 3 | 72 |
| 4 | 12 |
| 5 | 0 |

| b) Methylurea | |
|---|---|
| methylurea (mole/l.) | activity (%) |
| 0.5 | 22 |
| 1 | 174 |
| 1.5 | 313 |
| 2 | 375 |
| 2.5 | 332 |
| 3 | 215 |
| 4 | 12 |
| 5 | 0 |

| c) Ethylurea | |
|---|---|
| ethylurea (mole/l.) | activity (%) |
| 0.5 | 46 |
| 1 | 212 |
| 1.5 | 323 |
| 2 | 300 |
| 2.5 | 107 |
| 3 | 19 |

-continued

| | |
|---|---|
| 4 | 0 |
| 5 | 0 | d) Dimethylurea

| dimethylurea (mole/l.) | activity (%) | stimulatability (factor) |
|---|---|---|
| 0.5 | 167 | 8.8 |
| 1 | 256 | 8.9 |
| 1.5 | 283 | 9.4 |
| 2 | 177 | 7.7 |
| 2.5 | 78 | 8.9 |
| 3 | 23 | 9.9 |
| 4 | 4 | 8.6 |
| 5 | 2 | 3.5 |

3. Dependency of the activation yield upon the addition of fatty acid amides:

Reoxidation in 0.1 mole/l. tris (pH 10.5), 1 mmole/l. EDTA, 1 mg./ml. BSA, 5 mmole/l. GSH, 0.2 mmole/l. GSSG.

a) Formamide

| formamide (mole/l.) | activity (%) |
|---|---|
| 0 | 42 |
| 0.5 | 59 |
| 1 | 175 |
| 1.5 | 245 |
| 2 | 325 |
| 2.5 | 423 |
| 3 | 444 |
| 4 | 416 |
| 5 | 341 | b) Methylformamide

| methylformamide (mole/l.) | activity (%) |
|---|---|
| 0.5 | 100 |
| 1 | 135 |
| 1.5 | 304 |
| 2 | 389 |
| 2.5 | 466 |
| 3 | 452 |
| 4 | 425 |
| 5 | 121 | c) Acetamide

| acetamide (mole/l.) | activity (%) |
|---|---|
| 0.5 | 72 |
| 1 | 134 |
| 1.5 | 207 |
| 2 | 261 |
| 2.5 | 204 |
| 3 | 237 |
| 4 | 198 |
| 5 | 141 | d) Propionamide

| propionamide (mole/l.) | activity (%) |
|---|---|
| 0.5 | 95 |
| 1 | 99 |
| 1.5 | 197 |
| 2 | 150 |

-continued

| | |
|---|---|
| 2.5 | 101 |
| 3 | 39 |
| 4 | 2 |
| 5 | 0 | e) Butyramide

| butyramide (mole/l.) | activity (%) |
|---|---|
| 0.5 | 55 |
| 1 | 52 |
| 1.5 | 17 |
| 2 | 0 |

4. Dependency of the activation yield on the pH value
Reoxidation in 0.1 mole/l. tris/HCl+1 mmole/l. EDTA
+0.5 mole/l. L-arginine
+1 mg./ml. BSA
+0.5 mmole/l. GSH
+0.5 mmole/l. GSSG

| pH | activity (%) | stimulatability (factor) |
|---|---|---|
| 7 | 1 | — |
| 8 | 22 | 3.0 |
| 9 | 89 | 13.6 |
| 10 | 105 | 20.3 |
| 11 | 95 | 21.3 |

5. Dependency of the activation yield upon the GSH/GSSG concentration
Reoxidation in 0.1 mole/l. tris/HCl, pH 10.5
+1 mmole/l. EDTA
+0.5 mole/l. L-arginine
+1 mg./ml. BSA a) + 1 mmole/l. GSH

| (GSSG) (mmole/l.) | activity (%) | stimulatability (factor) |
|---|---|---|
| 0.1 | 239 | 14.9 |
| 0.2 | 273 | 15.3 |
| 0.5 | 193 | 13.3 |
| 1 | 198 | 12.5 |
| 5 | 17 | 2.1 |
| 10 | 0 | — |
| 20 | 0 | — | b) + 0.2 mmole/l. GSSG

| (GSH) (mmole/l.) | activity (%) | stimulatability (factor) |
|---|---|---|
| 0.05 | 15 | 2.2 |
| 0.1 | 40 | 3.8 |
| 0.2 | 112 | 6.8 |
| 0.5 | 142 | 7.4 |
| 1 | 273 | 6.8 |
| 5 | 260 | 7.9 |
| 10 | 143 | 6.3 |
| 20 | 55 | 5.1 |

6. Dependency of the activation yield upon the protein concentration in the case of the reoxidation (dilution 1:20–1:500)
Reoxidation on 0.1 mole/l. tris/HCl (pH 10.5)

+1 mmole/l. EDTA
+0.5 mole/l. L-arginine
+1 mg./ml. BSA
+0.5 mmole/l. GSH
+0.5 mmole/l. GSSG

| dilution | activity (%) | stimulatability (factor) |
|---|---|---|
| 1:10 | 29 | 15.3 |
| 1:20 | 45 | 25.4 |
| 1:50 | 69 | 37.9 |
| 1:100 | 100 | 37.9 |
| 1:200 | 79 | 52.7 |
| 1:500 | 29 | 28.7 |

7. Dependency of the activation yield upon the addition of BSA

Reoxidation in 0.1 mole/l. tris/HCl (pH 10.5)
+1 mmole/l. EDTA
+0.5 mole L-arginine
+0.5 mmole/l. GSH
+0.5 mmole/l. GSSG

| BSA (mg./ml.) | activity (%) |
|---|---|
| 0 | 47 |
| 0.5 | 83 |
| 1 | 100 |
| 3 | 102 |
| 5 | 52 |

Figure 2:
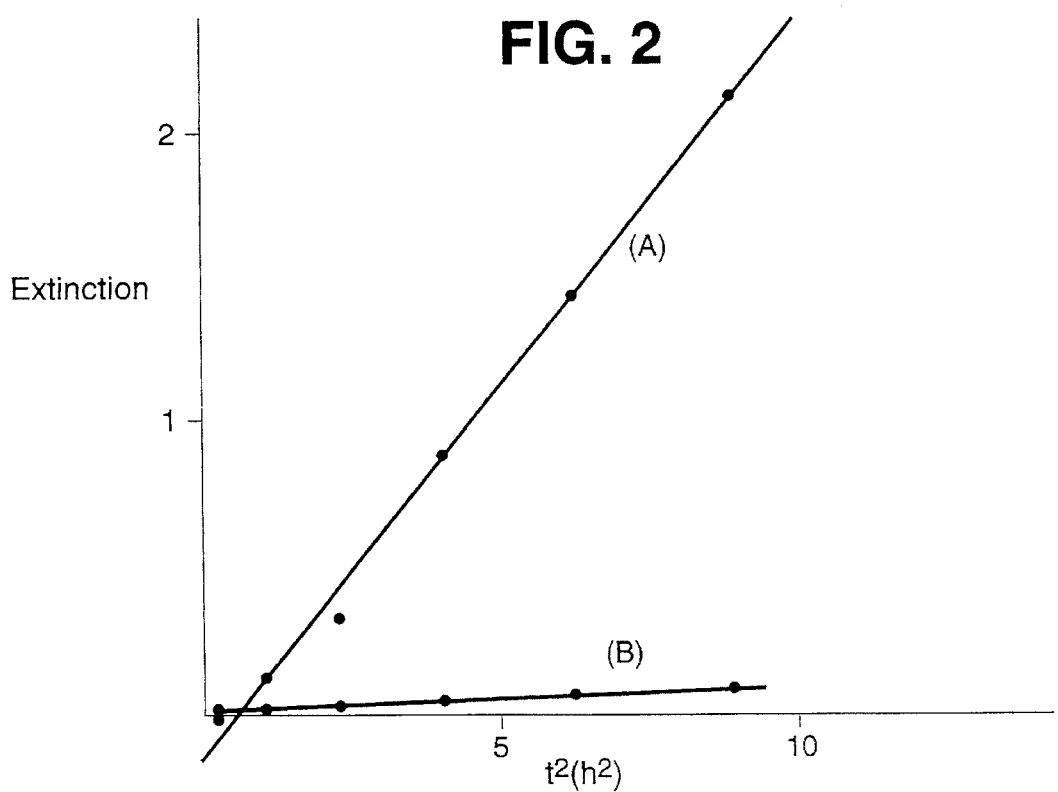
FIG. 2 shows, in line A, the activity of TPA in the presence of CNBr-FCP in a standard assay and in line B, the activity of TPA in the absence of CNBr-FCP.

The FIGS. 1 and 2 show the activity with and without CNBr-FCP in the standard test after 17 hours reoxidation at room temperature in 0.1 mole/l. tris/HCl (pH=10.5)+1 mmole/l. EDTA+0.5 mole/l. L-arginine+ 1 mg./ml. BSA+ 0.5 mmole/l. GSH+0.5 mmole/l. GSSG. In the FIGS. 1 and 2, the curves (A) signify the activity in the presence of CNBr-FCP, the curves (B) the activity without CNBr-FCP.

EXAMPLE 4

Activation of t-PA via the Mixed Disulphides of t-PA and Glutathione

The "refractile bodies" used were obtained according to one of the preceding Examples. The reduction of the "refractile bodies" was carried out by 2 hours incubation at room temperature in 0.1 mole/l. tris/HCl, pH 8.6, 1 mmole/l. EDTA, 6 mole/l. Gdn. HCl, 0.2 mole/l. DTE at a protein concentration of about 1 mg./ml.

The reduced protein dialysed against 0.01 mole/l. HCl was diluted in the ratio of 1:1 with 0.1 mole/l. tris, pH 9.3, 9 mole/l. urea and 0.2 mole/l. GSSG and incubated for 5 hours at room temperature.

After acidification with conc. HCl to pH 3, there took place dialysis against 0.01 mole/l. HCl at 4° C. After the dialysis, the total protein concentration amounted to 0.33 mg./ml. The optimum reactivation conditions were determined with the so-prepared t-PASSG.

a) pH Optimum of the Activation of t-PASSG

Here, as in the following optimising experiments, there was (1) used no GSSG and (2) the activation was determined after 17 hours incubation at room temperature. Activation took place by a 1:100 dilution in 0.1 mole/l. tris, 1 mmole/l. EDTA, 0.5 mole/l. L-arginine, 1 mg./ml. BSA and 2 mmole/l. GSH with variation of the pH value.

| pH | yield (%) | stimulatability |
|---|---|---|
| 6 | 0.04 | 3.3 |
| 6.5 | 0.37 | 9.5 |
| 7 | 1.35 | 11.4 |
| 7.5 | 5.66 | 7.1 |
| 8 | 7.32 | 8.2 |
| 8.5 | 8.65 | 7.0 |
| 9 | 8.59 | 8.7 |
| 9.5 | 8.32 | 11.7 |
| 10 | 6.15 | 12.5 |
| 10.5 | 3.07 | 11.2 |

The yield was determined in % of active t-PA, referred to the amount of protein used.

b) Reproducibility of the Results of the Activation of t-PASSG

In the case of identical activation conditions, in the case of different measurement series there are observed different yields which, inter alia, are caused by variations of the standard t-PA's. For the clarification of the breadth of error, all activation data after 1:100 or 1:200 dilution in 0.1 mole/l. tris/HCl, pH 8.5, 1 mmole/l. EDTA, 0.5 mole/l. L-arginine, 1 mg./ml. BSA and 2 mmole/l., GSH, are assembled.

| experiment | yield (%) | stimulatability |
|---|---|---|
| 1 | 8.65 | 7.0 |
| 2 | 4.47 | 9.3 |
| 3 | 4.49 | 9.7 |
| 4 | 8.50 | 6.5 |
| 5 | 3.45 | 17.2 |
| 6 | 4.32 | 8.3 |
| 7 | 3.29 | 14.0 |
| 8 | 3.54 | 13.4 |
| 9 | 5.07 | 16.4 |
| average value | 5.1 +/- 1.9 | 11.3 +/- 3.8 | c) Stability of the activated protein

Activation took place in the said Example by a 1:200 dilution in 0.1 mole/l. tris/HCl, 1 mmole/l. EDTA, 0.5 mole/l. L-arginine, 1 mg./ml. BSA and 2 mmole/l. GSH,

| time | pH 9.5 | |
|---|---|---|
| (h.) | yield (%) | stim. |
| 1 | 0 | — |
| 6 | 0.89 | 15.5 |
| 23 | 2.43 | 23.1 |
| 47 | 2.83 | 23.6 |
| 71 | 2.62 | 21.5 |
| 215 | 2.21 | 22.6 |
| 239 | 2.28 | 14.3 |

EXAMPLE 5

Activation of Gene-technologically Produced Interferon-β

"Refractile bodies" were produced according to the previously mentioned methods. The reduction/solubilisation of the "refractile bodies" was carried out as follows: The pellet was incubated for 3 hours at 25° C. in 10 ml. 9.1 mole/l.

tris/HCl, pH 8.6, 6 mole/l. Gdn.HCl, 1 mmole/l. EDTA and 0.2 mole/l. DTE and after 30 minutes centrifuging at 4° C. and 48000 g, the pH of the supernatant was adjusted to about 3 with concentrated HCl. Subsequently, there was carried out s gel filtration over Sephadex G25F in 0.01 mole/l. HCl.

The eluate was investigated for conductivity, protein concentration and reactivatability.

The activity of the reoxidised protein refers to a "standard activation" (=100%) in 0.1 mole/l. tris/HCl, pH 10.5, 1 mmole/l. EDTA, 5 mmole/l. GSH, 0.5 mmole/l. GSSG and 0.25 mole/l. L-arginine.

a) Dependency of the activation yield on the addition of L-arginine

The eluate was diluted 1:50 with 0.1 mole/l. tris/HCl, pH 8.5, 1 mmole/l. EDTA, 5 mmole/l. GSH, 0.5 mmole/l. GSSG and activated for 20 hours at 0° C.

| L-Arginine dependency of the activation | |
|---|---|
| L-arginine (mole/l.) | activity (%) |
| 0 | 8 |
| 0.25 | 8 |
| 0.5 | 15 |
| 0.75 | 15 | b) Dependency of the activation yield on the addition of urea

The activation solution corresponded to that of point a) but it was activated for 17 hours at 0° C.

| Urea dependency of the activation | |
|---|---|
| urea (mole/l.) | activity (%) |
| 0 | 13 |
| 0.5 | 100 |
| 1 | 200 |
| 1.5 | 100 | c) Dependency of the activation yield upon the addition of formamide

Activation as in a); the samples were investigated after 17 hours activation at 0° C.

| Formamide dependency of the activation | |
|---|---|
| formamide (mole/l.) | activity |
| 0 | 13 |
| 1 | 13 |
| 2 | 13 |
| 3 | 0 |
| 4 | 0 | d) Dependency of the activation yield on the redox buffer

The eluate was diluted 1:50 in 0.1 mole/l. tris/HCl, pH 8.5, 1 mmole/l. EDTA and 0.25 mole/l. L-arginine and the samples investigated after 17 hours activation at 0° C.

| GSH/GSSG dependency of the activation | | |
|---|---|---|
| GSH (mmole/l.) | GSSG (mmole/l.) | activity (%) |
| 1 | 0.5 | 6 |
| 5 | 0.5 | 13 |
| 10 | 0.5 | 25 |
| 20 | 0.5 | 25 |
| 5 | 0.1 | 13 |
| 5 | 0.5 | 13 |
| 5 | 1.0 | 13 |
| 5 | 5 | 6 | e) Dependency of the activation yield on the addition of BSA

The eluate was diluted 1:50 in 0.1 mole/l. tris/HCl, pH 8.5, 1 mmole/l. EDTA, 5 mmole/l. GSH, 0.5 mmole/l. GSSG and 0.25 mole/l. L-arginine and investigated after 17 hours activation at 0° C.

| BSA dependency of the activation | |
|---|---|
| BSA (mg./ml.) | activity (%) |
| 0 | 13 |
| 1 | 13 |
| 2 | 25 |
| 5 | 13 | f) Dependency of the activation yield on the pH

The eluate was diluted 1:50 in 0.1 mole/l. tris/HCl, 1 mmole/l. EDTA, 5 mmole/l. GSH, 0.5 mmole/l. GSSG and 0.25 mole/l. L-arginine and investigated after 17 hours activation at 0° C.

| pH dependency of the activation | |
|---|---|
| pH | activity (%) |
| 6.5 | 0 |
| 7.5 | 6 |
| 8.5 | 13 |
| 9.5 | 50 |
| 10.5 | 100 |

EXAMPLE 6 (Renaturation of Antibody Fragments)

Expression of antibody fragments in *E. coli*

6.1 Construction of a plasmid for expressing the mAb MAK33 kappa chain in *E. coli*

The cloning of the kappa-cDNA of MAK33 as a PstI-fragment in pBR322 has been described (Buckel, P., et al. (1987), Gene 51, 13–19). By means of the restriction endonuclease Mnl I the cDNA was cut in direct 5'-position of the first amino acid codon of the mature kappa chain and cloned by means of an adapter (5'CATG3' hybridized with 5'CAT-GAATT3') as an EcoRI-PstI-fragment into the vector pKK223-3, DSM 3694P (Brosius et al. (1981), Plasmid 6, 112–118) which had also been cut with EcoRI and PstI. For shortening the 3'-untranslated range of the cDNA the resulting plasmid was opened by means of PstI, nucleolytically shortened with Bal31 and, subsequently, the EcoRI-Bal31-fragment corresponding to the kappa-cDNA was cloned back into the EcoRI HindIII cut vector pKK223-3 by means of a HindIII-linker. The resulting plasmid is referred to as pBT111 (FIG. 3 shows the sequence of the expression plasmid; kappa from nucleotide position 7 to 663).

6.2 Construction of a plasmid for expressing the Fd-fragment of the gamma chain of MAK33 in *E. coli*

The cloning of the MAK33 gamma-cDNA as a PstI-fragment in pBR322 has also been described (Buckel et al. 1987). For the purpose of expression an XmaI-restriction site was introduced directly before the first amino acid of the mature gamma chain by oligonucleotide directed mutagenesis. A gamma-Fd-fragment was created by means of the same technique by introducing a stop codon behind amino acid position 225, whereby additionally a BclI and a SalI-restriction site were introduced. The resulting XmaI-SalI-fragment, which codes for the gamma-Fd-fragment, was cloned into pUC8 (Vieira+Messing (1982) Gene 19, 259–268). FIG. 4 shows the sequence of the expression plasmid p10169 formed (gamma-Fd from nucleotide position 240 to 917).

6.3 Expression of the Antibody Chains in *E. coli*

Expression plasmids pBT111 and p10169 were transformed each individually in *E. coli* (DSM 3689), which furthermore contained a plasmid for the expression of the lac-repressor (lacI$^q$) in trans. The *E. coli* cells were cultured on LB-medium to reach an optical density $OD_{550\ nm}= 0.5$, then induced with 1 g/l isopropyl-β-D-thiogalactoside (IPTG) and incubated for another 4 hours at 37° C. Subsequently, the cells were centrifuged off.

6.4 Preparation of the "inclusion bodies"

To this end, about 25 g *E. coli* (cf. Example 6.3) moist cell mass per immunoglobulin chain were taken up in 580 ml 0.1 mole/l Tris HCl, pH 6.5, 20 mmole/l EDTA and the cells were homogenized with a shearing rod (Ultraturax). Subsequently, 0.25 mg/ml lysozyme were added, incubated for 30 minutes at room temperature and then suspended in 0.5 mole/l NaCl, 5% v/v Triton-X-100 and homogenized with a shearing rod (Ultraturax) and stirred for another 30 minutes at room temperature. Subsequently, centrifugation was carried out in a Sorvall GSA-rotor for 50 minutes at 4° C. and 13,000 rpm. The pellets were taken up in 300 ml 0.1 mole/l Tris HCl, pH 6.5, 20 mmole/l EDTA, 2.5% v/v Triton-X-100 and homogenized. Then a further centrifugation was carried out for 30 minutes at 4° C. and 13,000 rpm, again in a Sorvall GSA-rotor. The pellets were taken up in 300 ml 0.1 mole/l Tris HCl, pH 6.5, 20 mmole/l EDTA, 0.5% v/v Triton-X-100 and homogenized. Subsequently, there were carried out another two centrifugations for 30 minutes each at 4° C. and 13,000 rpm in a Sorvall GSA-rotor and, after each centrifugation, the pellets were taken up in 300 ml and 250 ml, respectively, 0.1 mole/l Tris HCl, pH 6.5, 20 mmole/l EDTA and homogenized.

6.5 Detection of the inhibiting activity of the monoclonal antibodies

MAK33 IgG recognizes an epitope which is formed only on the M sub-units of the skeleton muscle specific isoenzyme CK-MM. Through binding to the epitope the enzymatic activity is inhibited by 80% (P. Buckel et al., 1987). Thus, the CK-MM inhibition test is a very convincing test for the detection of the reconstitution of MAK33 after complete denaturation and reduction, since only a completely renatured antigen binding site is capable of inhibiting the enzyme.

The activity of the creatine kinase was determined by means of a coupled enzymatic test of Boehringer Mannheim GmbH (H. U. Bergmeyer, Meth. of Enzym. Analysis, 3rd Edition, Vol. III, 510–540), whereby creatine kinase reacts creatine phosphate and ADP to give creatine and ATP. To obtain a spectroscopically detectable reaction the ATP formed is consumed by the hexokinase for the phosphorylation of glucose to give glucose-6-phosphate. Glucose-6-phosphate is oxidized by the glucose-6-phosphate dehydrogenase to give gluconate-6-phosphate, with $NADPH+H^+$ being formed from $NADP^+$. The activity of creatine kinase can be calculated from the change of extinction per minute.

From a calibration curve with native antibody against CK-MM the amount of native material can be determined, which corresponds to the inhibiting action in the renaturing batch. The amount of protein having inhibitory activity, related to the total amount of protein in the renaturing batch, represents the percentage yield of antibodies having inhibitory activity.

6.6 Solubilisation/reduction of the "refractile bodies"

"Refractile bodies" of the individual chains were incubated separately at a protein concentration of 4–6 mg/ml in 0.1 mole/l Tris-HCl (pH 8.6), 6 mole/l guanidine hydrochloride, 0.3 mole/l DTE and 2 mmole/l EDTA for 3 hours at room temperature. Subsequently, insoluble material (cell wall fragments etc.) were centrifuged off (e.g. for 30 min at 17,000 g, 4° C.). The pH of the supernatant was adjusted to pH 3 with concentrated HCl. Subsequently, reduction agent and buffer components were separated off by dialysis against 6 mole/l guanidine hydrochloride, pH 2, 4° C.

The thus obtained preparation of reduced denatured protein is either used directly for renaturation (cf.6.7) or first derivatized by means of glutathione disulfide (GSSG) to give a mixed disulfide and then renatured (cf. 6.8).

6.7 Dependency of renaturation on the arginine concentration in the renaturing buffer The solutions of the denatured, reduced individual chains were mixed at a mole ratio of 1:1 and then renatured by a 1:100 dilution in 0.1 mole/l Tris-HCl, 2 mmole/l EDTA, 1 mmole/l GSH, 1 mmole/l GSSG and increasing concentration of L-arginine at pH 9. The protein concentration was 60 µg/ml, the temperature 20° C. and the renaturation time 120 hours.

TABLE 1

Dependency of the renaturation of MAK33 Fab on arginine

| Arginine (mole/l) | Renaturation (%) |
|---|---|
| 0 | 4.0 |
| 0.1 | 6.5 |
| 0.2 | 8.3 |
| 0.3 | 9.3 |
| 0.4 | 10.0 |
| 0.5 | 9.7 |
| 0.6 | 8.8 |
| 0.7 | 7.3 |
| 0.8 | 5.9 |
| 0.9 | 4.1 |
| 1.0 | 3.6 |

6.8 Renaturation after derivatisation of the individual chains to give mixed disulfides The solutions of the denatured reduced individual chains in 6 mole/l guanidine hydrochloride, pH 2 were adjusted with GSSG to 0.1 mole/l and with Tris to 0.1 mole/l. Subsequently, the pH was ajusted to pH 8.5 with NaOH. After 2 hours of incubation at room temperature oxidation agent and buffer components were separated off by means of a dialysis against 6 mole/l guanidine hydrochloride, pH 2 at 4° C.

The solutions of the denatured, oxidized individual chains ("mixed disulfides") were mixed at a mole ratio of 1:1 and then renatured by a 1:100 dilution in 0.1 mole/l Tris-HCl, 0.3 mole/l arginine, 2 mmole/l EDTA and increasing concentration of GSH at pH 7. The protein concentration was 60

μg/ml, the temperature 20° C. and the renaturation time 120 hours.

TABLE 2

| Dependency of the renaturation of MAK33 Fab on GSH | |
|---|---|
| GSH (mmole/l) | Renaturation (%) |
| 0 | 0 |
| 0.1 | 11.9 |
| 0.2 | 12.4 |
| 0.3 | 13.0 |
| 0.5 | 12.5 |
| 0.7 | 9.7 |
| 1 | 8.8 |
| 2 | 5.4 |
| 4 | 2.5 |
| 7 | 0.3 |
| 10 | 0 |

EXAMPLE 7

Activation of Denatured Antibodies

The fab fragment of a monoclonal antibody, which is directed against creatine kinase (CK-MM) and can be produced from hybridoma cell line ECACC 88091404, is incubated in 0.1 mole/l Tris HCL, pH 8.5, 6 mole/l guanidine HCl, 2 mmole/l EDTA and 0.3 mole/l DTE for two hours at room temperature and at a concentration of 6 μg/ml and thereby denatured.

This solution containing the denatured antibody is diluted 1:100 with renaturing buffer (0.1 mole/l Tris HCl, pH 8.5, 0.5 mole/l L-aginine, 10 mmole/l GSSG, 2 mmole/l EDTA) and incubated for 200 hours at 20° C.

The yield of renatured antibody is 20%.

Renaturation was checked by determining the binding capacity of the antibody to CK-MM.

The activity of creatine kinase was determined by means of a coupled enzymatic test of Boehringer Mannheim GmbH (H. U. Bergmeyer, Meth. of Enzym. Analysis, 3rd Edition, Vol. III, 510– 540), whereby creatine kinase reacts creatine phosphate and ADP to give creatine and ATP. To obtain a spectroscopically detectable reaction, the ATP formed is consumed by hexokinase for the phosphorylation of glucose to give glucose-6-phosphate. Glucose-6-phosphate is oxidized by glucose-6-phosphate dehydrogenase to give gluconate-6-phosphate, with NADPH and $H^+$ being formed from $NADP^+$. The activity of creatine kinase can be calculated from the change of extinction per minute. From a calibration curve with native antibody against CK-MM the amount of native material can be determined, which corresponds to the inhibitory action in the renaturing batch. The amount of protein having inhibitory activity, related to the total amount of protein in the renaturing batch, represents the percentage yield of antibodies having inhibitory activity.

EXAMPLE 8 (Renaturation of a Tissue Plasminogen Activator Derivative)

8.1 Construction of plasmid pA27.3

The starting plasmid pREM7685 described in EPA 0 242 836 contains the following components: tac-promotor, lac-operator region with an ATG start codon, the region coding for the t-PA derivative FK2P, the transcription terminator from pKK223-3, a β-lactamase gene, a kanamycin resistance gene and the origin of the plasmid pACYC177, a plasmid which is present in the cell at a small copy number.

The sequence of the t-PA derivative FK2P is composed of the nucleotides 190–336 (F-domain), 717–1809 (K2-domain, protease, small amount of 3'UT) and an ATG start codon. The nucleotide positions are given according to the sequence described by Pennica et al., Nature 301 (1983) 214–221.

The deletion of the F-domain from the FK2P construction in plasmid pREM7685 was carried out essentially according to the method of Morinaga et al., Biotechnology 21 (1984), 634. For heteroduplex formation two fragments were isolated from pREM7685. Fragment A: pREM7685 was cleft with the restriction enzyme EcoRI. The cleavage products were separated by gel electrophoresis and the largest EcoRI-fragment was eluted from the gel. Fragment B: plasmid pREM7685 was linearized with the restriction enzyme XhoI. The linearized plasmid was also obtained preparatively after gel electrophoresis. For mutagenesis the following oligonucleotide was synthetically produced:

5' TG TCT TAC CAA GGA AAC AGT GA 3'

In order to form the heteroduplex fragment A, fragment B (450 fmole each) and the oligonucleotide (75 pmole) were mixed and incubated initially for three minutes in the presence of 50 mmole/l NaCl, 10 mmole/l Tris-HCl, pH 7.5 and 10 mmole/l $MgSO_4$ at 100° C. and immediately transferred to ice. The renaturation of the DNA was effected for 30 minutes at 60° C. For repair synthesis the following was added to the heteroduplex:

deoxynucleotide triphosphates (0.25 mmole/l), ATP (1 mmole/l), NaCl (100 mmole/l), Tris-HCl, pH 7.5 (6.5 mmole/l), $MgCl_2$ (8 mmole/l), β-mercaptoethanol (1 mmole/l), Klenow fragment of the DNA polymerase from E. coli (0.125 U/μl batch) and T4 ligase (0.1 U/μl batch). Repair synthesis was effected for 4 hours at 16° C. Subsequently, this batch was transformed in E. coli cells (RM82, DSM 3689) with a lac $I^q$ plasmid and the transformants were selected by adding 25 μg/ml kanamycin to the culture medium.

By means of the colony hybridisation technique using the above-described mutagenesis oligonucleotide as a probe those clones could be elected which carry the plasmid pA27.3. This plasmid differs from the starting plasmid pREM7685 inter alia by the absence of a PstI- and a SspI-restriction site, respectively. These two restriction sites are contained in that region of the starting plasmid which codes for the F-domain. The construction of the plasmid pA27.3 is shown schematically in FIG. 5

8.2 Preparation of active K2P from E. coli

Cell lysis and preparation of the inclusion bodies (IB's)

1.6 kg moist cell mass (E. coli, DSM 3689) were suspended in 10 l 0.1 mole/l Tris-HCl, 20 mmole/l EDTA, pH 6.5, 4° C. 2.5 g lysozyme were added to this and incubated for 30 minutes at 4° C.; subsequently complete cell digestion was carried out by means of high pressure dispersion. The digestion solution was mixed with 5 10.1 mole/l Tris-HCl, 20 mmole/l EDTA, 6% Triton X100 and 1.5 mole/l NaCl, pH 6.5 and incubated for another 30 minutes at 4° C. This was followed by the separation of the insoluble components (IB's) by centrifugation with a Padberg centrifuge. The pellet was suspended in 10 l 0.1 mole/l Tris-HCl, 20 mmole/l EDTA, pH 6.5, incubated for 30 minutes at 4° C. and IB preparation was isolated by subsequent centrifugation.

8.3 Activity determination

The in vitro activity of K2P from E. coli was determined according to the test instructions in "Zeitschrift für die gesamte innere Medizin" (ZGIMAL) 42 (17) 478–486 (1987). The specific activity was 550,000 IU/mg ±200,000

IU/mg. The stimulatability of K2P from *E. coli* by BrCN fragments of the fibrinogen (activity in the presence of fibrinogen fragments divided by activity without fibrinogen fragments) was >25 in this test system.

8.4 Solubilisation/Reduction of the "refractile bodies"

"Refractile bodies" were incubated at a protein concentration of 4–6 mg/ml in 0.1 mole/l Tris-HCl (pH 8.6), 6 mole/l guanidine hydrochloride, 0.3 mole/l DTE and 2 mmole/l EDTA for 3 hours at room temperature. Then insoluble material (cell wall fragments etc.) was centrifuged off (e.g. for 30 min at 17,000 g, 4° C.). The pH of the supernatant was adjusted to pH 3 with concentrated HCl.

This was followed by separating off reduction agent and buffer components by dialysis against 6 mole/l guanidine hydrochloride, pH 2, 4° C.

8.5 Derivatisation to give mixed disulfide

The solution of the denatured, reduced protein in 6 mole/l guanidine hydrochloride, pH 2 was adjusted to 0.1 mole/l with GSSG and to 0.1 mole/l with Tris. Subsequently, the pH was adjusted to pH 8.5 with NaOH. After 2 hours of incubation at room temperature oxidation agent and buffer components were separated off by dialysis against 6 mole/l guanidine hydrochloride, pH 2, at 4° C.

8.6 Dependency of the renaturation of K2P on the arginine concentration in the renaturing buffer The solution of the denatured, oxidized protein ("mixed disulfide") was renatured by a 1:100 dilution in 0.1 mole/l Tris-HCl, 0.5 mmole/l GSH, 2 mmole/l EDTA and increasing concentration of L-arginine at pH 8.5. The protein concentration was 60 μg/ml, the temperature was 20° C. and the renaturing time 24 hours.

TABLE 3

Dependency of the renaturation of K2P on arginine

| Arginine (mole/l) | Renaturation (%) |
|---|---|
| 0 | 0 |
| 0.1 | 1.5 |
| 0.2 | 3.6 |
| 0.3 | 8.1 |
| 0.4 | 11.9 |
| 0.5 | 16.3 |
| 0.6 | 18.2 |
| 0.7 | 20.5 |
| 0.8 | 22.0 |

8.7 Dependency of the renaturation of K2P on the pH of the renaturing buffer

The solution of the denatured, oxidized protein ("mixed disulfide") was renatured by a 1:100 dilution in 0.1 mole/l Tris-HCl, 0.8 mole/l L-arginine, 0.5 mmole/l GSH, 2 mmole/l EDTA, with variation of the the pH. The protein concentration was 60 μg/ml, the temperature was 20° C. and the renaturing time 24 hours.

TABLE 4

Dependency of the renaturation of K2P on the pH

| pH | renaturation (%) |
|---|---|
| 6 | 1.0 |
| 7 | 4.3 |
| 7.5 | 7.3 |
| 8 | 11.1 |
| 8.5 | 21.0 |
| 9 | 17.0 |
| 10 | 5.1 |

We claim:

1. A process for activating a tissue type plasminogen activator molecule, comprising:
   (i) expressing said tissue type plasminogen activator molecule in a prokaryote to form refractile bodies;
   (ii) digesting prokaryotic cells which contain said refractile bodies;
   (iii) solubilizing said refractile bodies under conditions which reduce and denature said molecule; and
   (iv) oxidizing said solubilized, reduced and denatured molecule by contact with (a) reduced glutathione (GSH)/oxidized glutathione (GSSG) at a pH of from 9 to 12, wherein GSH is at a concentration of from 0.01 to 20 mmol/liter, GSSG is at a concentration of from 0.01 to 3 mmol/liter, and (b) a denaturing agent present at a non-denaturing concentration, wherein said denaturing agent is selected from the group consisting of arginine, guanidine hydrochloride, and a compound of formula $R_2$—CO—$NRR_1$, wherein R and $R_1$ are H or $C_1$–$C_4$ alkyl, and $R_2$ is H, $NHR_1$, or $C_1$–$C_3$ alkyl; so as to activate said molecule.

2. A process for activating a recombinantly produced molecule selected from the group consisting of (a) a tissue type plasminogen activator molecule and (b) an IgG molecule, comprising:
   (i) expressing said molecule in a prokaryote, to form refractile bodies,
   (ii) digesting prokaryotic cells which contain said refractile bodies,
   (iii) solubilizing said refractile bodies with an agent which reduces and denatures said molecule,
   (iv) removing said agent,
   (v) adding oxidized glutathione (GSSG) to said solubilized, reduced, and denatured molecule, under denaturing conditions, so as to convert thiol groups in said molecule into mixed disulphides, and GSSG into glutathione,
   (vi) removing any unreacted GSSG, and
   (vii) oxidizing said solubilized, reduced, and denatured mixed disulphide containing molecule by adding reduced glutathione (GSH) at a concentration of from 0.5 mmole/liter to 5 mmole/liter, at a pH of from 7 to 10.5, and a non-denaturing concentration of a denaturing agent selected from the group consisting of arginine, guanidine hydrochloride, and a compound of formula $R_2$—CO—$NRR_1$, wherein R and $R_1$ are H or $C_1$–$C_4$ alkyl, and $R_2$ is H, $NHR_1$, $C_1$–$C_3$ alkyl; so as to activate said molecule.

3. The process of claim 1, wherein said GSH is at a concentration of from 0.2 mmole/liter to 10 mmole/liter, and said GSSG is at a concentration of from 0.05 to 1 mmole/liter.

4. The process of claim 1 or 2, further comprising purifying said molecule following solubilization but before oxidation.

5. The process of claim 1 or 2, further comprising adding a reactivation buffer which contains dithioerythriol following reduction and denaturing of said molecule.

6. The process of claim 1 or 2, wherein said prokaryote is selected from the group consisting of *Escherichia coli* and *Pseudomonas putida*.

7. The process of claim 1 or 2, wherein said denaturing agent is arginine or guanidine hydrochloride and is used at a concentration of from 0.1 to 1.0 mole/liter.

8. The process of claim 7, wherein said denaturing agent is used at a concentration of from 0.25 to 0.8 mole/liter.

9. The process of claim 1 or 2, wherein said denaturing agent is of formula $R_2$—CO—$NRR_1$ used at a concentration of from 0.5 to 4.0 mole/liter.

10. The process of claim 1 or 2, wherein said denaturing agent is used at a concentration of from 1 to 3.5 mole/liter.

11. The process of claim 1 or 2, comprising solubilizing said refractile bodies in the presence of a reducing agent that contains a mercapto group and a denaturing agent, at an alkaline pH.

12. The process of claim 1 or 2, wherein said denaturing agent is guanidine hydrochloride or a compound of formula $R_2$—CO—$NRR_1$, wherein R and $R_1$ are H or $C_1$–$C_4$ alkyl, and $R_2$ is H, $NHR_1$, or $C_1$–$C_3$ alkyl.

13. The process of claim 12, wherein said denaturing agent is guanidine hydrochloride at a concentration of 6 mole/liter.

14. The process of claim 12, wherein said denaturing agent is of formula $R_2$—CO—$NRR_1$, at a concentration of 8 mole/liter.

15. The process of claim 1 or 2, comprising solubilizing said refractile bodies in the presence of a member selected from the group consisting of dithioerythriol, β-mercaptoethanol, cysteine, and reduced glutathione.

16. The process of claim 1 or 2, wherein said denaturing agent is arginine or guanidine hydrochloride, at a concentration of from 0.25 to 8.0 mole/liter.

17. The process of claim 1 or 2, further comprising oxidizing said molecule in the presence of bovine serum albumin.

18. The method of claim 1 or 2, further comprising oxidizing said molecule in the presence of (ethylenedinitrilo) tetraacetic acid.

19. The process of claim 2, wherein said molecule is interferon-β.

20. The process of claim 2, further comprising separating mixed disulphide containing molecules and glutathione from GSSG and molecules not containing mixed disulphides via ion exchange.

* * * * *